US008131560B2

(12) United States Patent
Lawton et al.

(10) Patent No.: US 8,131,560 B2
(45) Date of Patent: Mar. 6, 2012

(54) SYSTEMS AND METHODS FOR MANAGING REGULATORY INFORMATION

(75) Inventors: Alison Lawton, Lexington, MA (US); Rachel Carle, Danvers, MA (US); Monica Mehta, Burlington, MA (US); Mary Durham, Groton, MA (US); Richard J. Granfield, Framingham, MA (US); James Earl Kiely, Medford, MA (US); David J. Puig, Hopkinton, MA (US)

(73) Assignee: Genzyme Corporation, Cambridge, MA (US)

( * ) Notice: Subject to any disclaimer, the term of this patent is extended or adjusted under 35 U.S.C. 154(b) by 1222 days.

(21) Appl. No.: 11/353,994

(22) Filed: Feb. 15, 2006

(65) Prior Publication Data

US 2007/0198477 A1 Aug. 23, 2007

(51) Int. Cl.
*G06Q 10/00* (2006.01)
*G06Q 50/00* (2006.01)
(52) U.S. Cl. .......................................................... 705/2
(58) Field of Classification Search .................. 705/4, 3; 707/3
See application file for complete search history.

(56) References Cited

U.S. PATENT DOCUMENTS

| | | | |
|---|---|---|---|
| 6,749,851 B2 * | 6/2004 | Mann et al. ................... | 424/94.6 |
| 7,085,800 B2 | 8/2006 | Abbott et al. | |
| 7,440,818 B2 * | 10/2008 | Handfield et al. ........... | 700/240 |
| 2001/0056359 A1 * | 12/2001 | Abreu ............................... | 705/3 |
| 2002/0023109 A1 | 2/2002 | Lederer, Jr. et al. | |
| 2002/0120477 A1 * | 8/2002 | Jinnett ............................... | 705/4 |
| 2002/0165806 A1 | 11/2002 | Kataria et al. | |
| 2003/0069894 A1 | 4/2003 | Cotter et al. | |
| 2003/0120532 A1 * | 6/2003 | Brumm et al. .................... | 705/9 |
| 2004/0041839 A1 | 3/2004 | Scher et al. | |
| 2004/0177326 A1 | 9/2004 | Bibko et al. | |
| 2005/0278308 A1 * | 12/2005 | Barstow ............................ | 707/3 |
| 2006/0025932 A1 * | 2/2006 | Dadala et al. ................... | 702/19 |
| 2006/0059137 A1 * | 3/2006 | Walker ............................... | 707/3 |
| 2006/0106847 A1 * | 5/2006 | Eckardt et al. ............... | 707/101 |
| 2006/0265273 A1 * | 11/2006 | Nottoli ............................ | 705/10 |
| 2007/0061393 A1 * | 3/2007 | Moore .......................... | 709/201 |

OTHER PUBLICATIONS

"ArisGlobal Releases Register 4, A Web-Based Tool to Help Life Science Organizations Protect Their Valuable Product Portfolios", Press Release of Apr. 14, 2005 (webpage accessed Nov. 10, 2006).

* cited by examiner

*Primary Examiner* — Gerald J. O'Connor
*Assistant Examiner* — Trang Nguyen
(74) *Attorney, Agent, or Firm* — Finnegan, Henderson, Farabow, Garrett & Dunner, LLP

(57) ABSTRACT

Systems, methods, and articles of manufacture are provided for managing regulatory data pertaining to a healthcare product. For example, the system may include a network interface for receiving, from a client terminal, a request for regulatory data related to regulatory activity about a product as it pertains to a regulatory authority. The system also includes interconnected information stores for storing regulatory data associated with the product, where the information stores may include: contact records associated with respective contacts with the regulatory authority; commitment records associated with respective commitments made to the regulatory authority; and product information records associated with respective documents associated with the product. The system also includes a processing module for identifying, in response to the received request, each contact record, commitment record, product information record, and central files record associated with the product related to the received request.

23 Claims, 13 Drawing Sheets

*(Screen layout showing sections)*

Section 500 (overall)

Section 510 — Top toolbar: Contact Reports | Commitments | Products | Central Files | RA Calendar | Global Search | Security | References | Reports Section 520 (left navigation):
- Product Information
- Synonyms
- Product Approvals
- Product Contacts
- Product Partners
- Conditional Allowances
- CMC Product Change
- CMC Reporting Requirements
- Product Application
- CMC Change Section 530 — Search: Product Name: [___] Product Category [Choose Product Family ▼]

Section 540 — Buttons: Add | Edit | Italics | Save | Cancel | Lock | Unlock | ? | Verify | Print | Help | Change History Fields:
- Product ID: [___]
- CF Product Number: [___]
- US Adopted Name: [___]
- Scientific Name: [___]
- Product Category: [Choose Product Family ▼]
- Product Name: [___]
- Trade Name: [___]
- Int Non Propriety Name: [___]
- Product Abbreviation: [___]
- Active: ☐

Section 550:
- Product Approvals
- Product Partners

| Contact Reports | Commitments | Products | Central Files | RA Calendar | Global Search | Security | References | Reports |

Search

New Record

Section 700

Section 710

Document ID: _____
Agency: [BA/FDA/CDER ▼]
Adverse Event Number: _____
Amendment to Supplement: _____
Date Bibliographic Data Entered: _____
Arrived Date: _____ 📅
Document Title: _____
File Number: _____
Number of CDs: _____
Physical Description: _____

Keywords: _____

Section 740

[Cancel] [Save]

Document URL: _____
Region/Country: [United States (12) ▼]
Amendment Number: _____
Date of Document: _____ 📅
Date Physical Item First Received: _____ 📅
Date Removed: _____ 📅
Document Type: [Contact Reports ▼]
Number of Volumes: _____
Old Document Number: _____
CF Special Instructions: _____

[Resume]

Figure 8(A):

[Screen layout rotated 90°, showing a Global Search interface]

- Top navigation buttons: Contact Reports | Commitments | Products | Central Files | RA Calendar | Global Search | Security | References | Reports
- Left panel: Global Search / Global Search Results
- Section 800 (main area), Section 810 (top nav), Section 830 (right area)
- 820 indicates the left panel Search panel fields:
- Query ID:
- Query Name:
- Buttons: Add | Edit | Italics | Save Query | Cancel | ? | ? | Help
- Query ID:
- Query Name:
- Agency Reference Number: [Choose Agency Reference]
- Agency: FDA
- Document Type: Application
- Application Type: Choose an Application
- From Date:
- To Date: 9/14/2004
- Product:
- Region/County: United Arab Emirates / United Kingdom / United Republic of Tanzania
- Free Text Search:

Figure 8(B):

Section 830

Free Text Search:

Result Name: _____ Result Description: _____

Selected Data Stores:
- ☐ Contact Reports  ☐ Product Information  ☐ RA Calendar
- ☐ Commitments  ☐ Central Files

Section 850

Contact Report Search

[Export to HTML]  [Export to Excel]

| Contact ID | Subject | Contact Date | Summary |

Commitment Search

[Export to HTML]  [Export to Excel]

| Commitment ID | Description | Close-out Comment |

SYSTEMS AND METHODS FOR MANAGING REGULATORY INFORMATION

BACKGROUND DESCRIPTION

1. Technical Field

The present invention generally relates to systems, methods, and computer readable media for managing regulatory information or data, and, more particularly, for managing regulatory data relating to the development and regulatory approval of a product.

2. Background

Market access is becoming more and more difficult in markets subject to product regulation, such as the healthcare environment. Pharmaceutical, biotechnology, and medical device companies are faced with high product development costs, tough competition, and extensive regulations. The rules and procedures for obtaining regulatory review and approval often change, as do the personnel within the regulatory agencies or authorities. At the same time, companies are under enormous pressure to obtain quick regulatory approval and to keep products in compliance.

Many of today's products require regulatory approval or authorization. For instance, pharmaceutical and biotechnology companies must obtain approval from a regulatory authority, such as the U.S. Food and Drug Administration (FDA), before a new drug can be marketed. Such companies may have regulatory affairs departments to manage all communications between the company and the various regulatory authorities with which it deals. The regulatory affairs department must also work with numerous other groups or divisions within the corporation, such as those responsible for quality control, research and development, and sales and marketing, to ensure that regulatory requirements are met in a coordinated fashion.

The volume of data that a regulatory affairs department must manage can be enormous. Indeed, a regulatory affairs department is often responsible for numerous products subject to regulation by a host of regulatory authorities throughout the world. The amount of regulatory data for such products can grow exponentially each year as communications with those authorities continue to evolve. Moreover, companies and regulatory authorities typically require that this regulatory data be kept readily available for authority inspections and business planning.

Often, however, the regulatory data is spread over various locations throughout a company. Persons within a regulatory affairs department must often use numerous individual manual systems to track data pertaining to the products for which they are responsible. Moreover, the regulatory data is often not easily tracked, accessed, or referenced with respect to a particular product. In such environments, locating collective information pertaining to key regulatory activities is complicated and enormously time-consuming.

Accordingly, there is a need for systems, methods, and articles of manufacture that can efficiently manage regulatory data in the healthcare industry. Moreover, there is a need for systems and methods that can manage regulatory data in the healthcare industry so that it can be tracked, e.g., with respect to a region, a particular product or group of products, a manufacturing site, a regulation, and so forth.

SUMMARY OF THE INVENTION

Consistent with embodiments of the present invention, systems, methods and computer readable media are disclosed for managing regulatory data In accordance with one embodiment, a system for managing regulatory data pertaining to a healthcare product is disclosed. The system may include a plurality of interconnected information stores, where each information store contains respective types of regulatory data associated with the healthcare product. The system may also include a processing module for identifying, in response to a received request, regulatory data about the healthcare product stored in the interconnected information stores.

It is to be understood that both the foregoing general description and the following detailed description (including drawings) are exemplary and explanatory only, and should not be considered restrictive of the scope of the invention, as described and claimed. Further, features and/or variations may be provided in addition to those set forth herein. For example, embodiments of the invention may be directed to various combinations and sub-combinations of the features described in the detailed description.

BRIEF DESCRIPTION OF THE DRAWINGS

The accompanying drawings, which are incorporated in and constitute a part of this disclosure, illustrate various embodiments and aspects of the present invention. In the drawings:

FIGS. 4(A) and 4(B) illustrate an exemplary user interface template for a regulatory contact report database, consistent with an embodiment of the present invention;

FIG. 5 illustrates an exemplary user interface template for a product information database, consistent with an embodiment of the present invention;

FIG. 6 illustrates an exemplary user interface template for a calendar database, consistent with an embodiment of the present invention;

FIGS. 7(A) and 7(B) illustrate exemplary user interface templates for a central files database, consistent with an embodiment of the present invention;

FIGS. 8(A) and 8(B) illustrate an exemplary user interface template for a global search function, consistent with an embodiment of the present invention.

DETAILED DESCRIPTION

Figure 1:
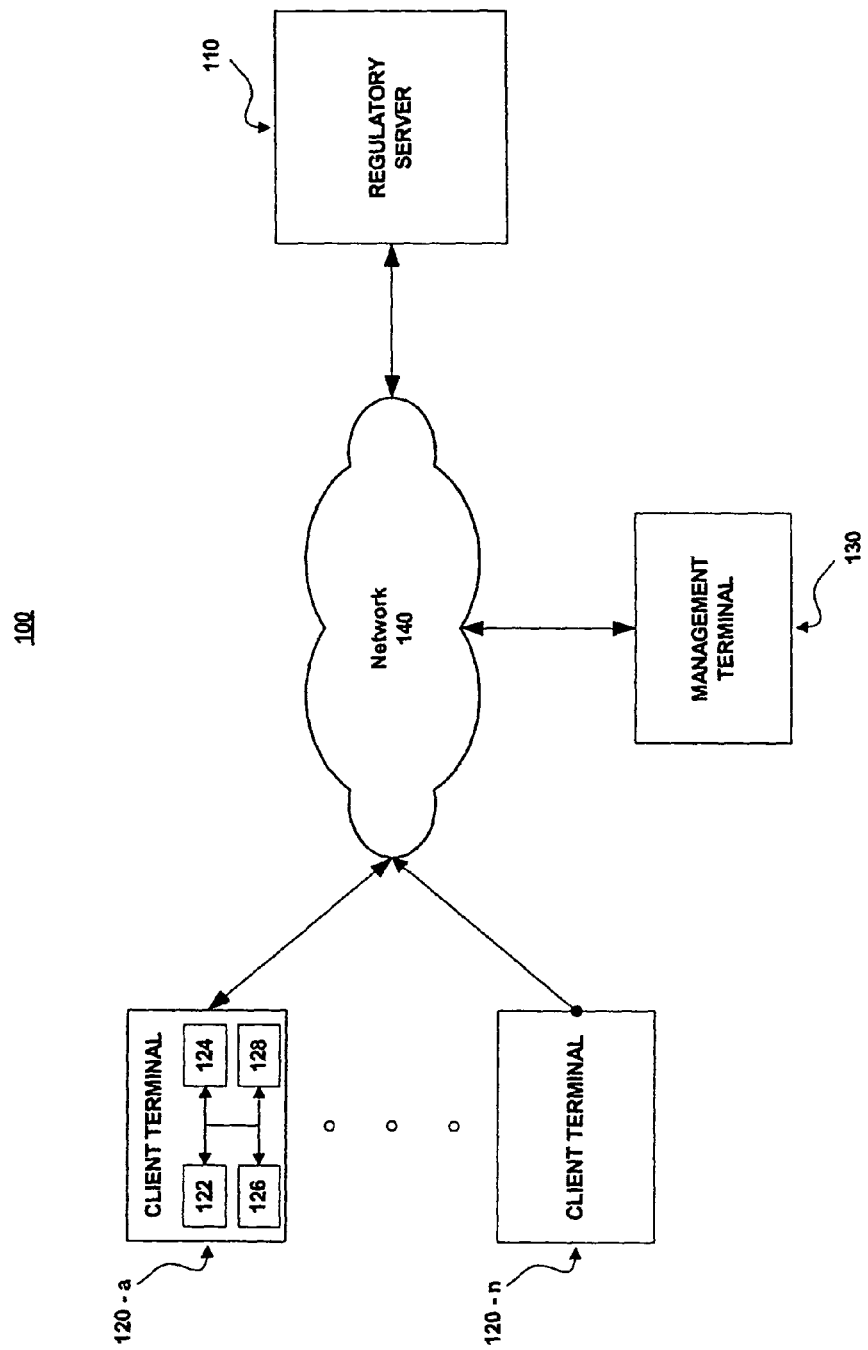
FIG. 1 is a diagram of an exemplary regulatory data management system consistent with an embodiment of the present invention.

Certain portions of the following detailed description refer to the accompanying drawings. Wherever possible, the same reference numbers are used in the drawings and the following description to refer to the same or similar parts. While several exemplary embodiments are described herein, modifications, adaptations and other implementations are possible, without departing from the spirit and scope of this disclosure. For example, substitutions, additions or modifications may be made to the components illustrated in the drawings, and the exemplary methods described herein may be modified by substituting, reordering, or adding steps to the disclosed methods. Accordingly, the following detailed description should not be limiting. Instead, the proper scope of this disclosure is defined first and foremost by the appended claims.

This invention relates to the processing, storage, access, and management of regulatory data pertaining to a healthcare product. Systems and methods consistent with the invention may manage regulatory data through interconnected information stores and a processing module. The information stores may be used to house two or more types of information. Such information may include, for example, records of contacts, commitments, calendar events, and/or product information. According to the invention, the information stores are interconnected so that data relationships among various types of regulatory information are established and accessed. In a preferred embodiment, the information stores may also include an indexing system referred to herein as central files records.

As used herein, the term "regulatory data" refers to any information associated with considering, seeking, obtaining, or maintaining approval from a regulatory authority to manufacture, use, sell, promote, import, export or store a product. In the case of a medicinal product, such regulatory authorities include, without limitation, the U.S. Health and Human Services (HHS), Food and Drug Administration (FDA), the European Medicines Evaluation Agency (EMEA), Ministries of Health (MHLW), Institutional Review Boards (IRBs) and the like.

As used herein, the term "product" refers to any type of healthcare good, service or process, the design, development, manufacture, use, storage or delivery of which is subject to governmental or institutional regulatory oversight. Products include, without limitation, goods and services related to therapeutics, diagnostics, medical devices, methods of treatment and diagnosis, etc.

As used herein, the term "manage" includes, without limitation, the activities of creating, processing, storing, interconnecting (linking), archiving, updating, accessing, standardizing, indexing, categorizing, searching, displaying, reporting, versioning, or controlling of data.

As used herein, the term "calendar records" refers to information pertaining to the scheduling of meetings, contacts and any other events of which the user may want to be aware. Examples of such information include without limitation, dates, times, locations, attendees, organizers, subject matter, etc. Such information may also contain links to internal documents or external websites that provide information pertinent to the scheduled event. In certain embodiments, calendar records contain one or more links enabling transfer of information from the calendar record to electronic calendars outside of the system.

As used herein, the term "contact records" refers to records of communications with regulatory contacts, and/or interactions between the user of the system and a regulatory authority. Contact records may include, without limitation, information such as: (1) the date, communication medium, and origin of each contact with a regulatory authority; (2) the product, manufacturing facility, or regulation to which the contact pertains; (3) the reason for the contact; (4) the region or country under discussion; (5) a summary of the discussion, (6) information identifying the persons associated with or involved in the regulatory contact and (7) a digital representation of the signature of the person responsible for signing the record. In preferred embodiments, and as described in more detail below, entry of data into an information store containing contact records may also prompt the entry of contact record data into a separate record such as a commitment record or central files record.

As used herein, the term "commitment records" refers to information pertaining to "commitments" made to a regulatory authority with respect to a product regulated by that authority. For example, a business entity may agree to perform certain types of product testing as a condition for obtaining approval from the regulatory authority. Accordingly, each commitment record may include information describing the commitment made by a user of the system, such as, for example: (1) a date the commitment was made, (2) the scope of the commitment, (3) a date the commitment was fulfilled, (4) information describing an anticipated resolution of the commitment, and/or (5) a final disposition of the commitment. The commitment record may include information describing a set of constituent tasks whose fulfillment constitutes completion of the commitment, and may facilitate management of those tasks. Further, the commitment record may be associated with a contact record describing any contact with the regulatory authority in making the commitment. A commitment record may also be linked to record(s) within, for example, an information store containing product information records, calendar records, or records from central files. In certain embodiments, commitment records contain one or more links enabling transfer of information from the commitment record to electronic calendars outside of the system.

As used herein, the term "product information records" refers to information associated with products of the business entity associated with the system. For instance, product information records may include records concerning: (1) naming of the product (including trade name, technical name, adopted name, etc.), (2) relationships with third parties pertaining to the development or commercialization of the product, (3) pending, accepted and/or approved applications to regulatory authorities, (4) manufacturing change requests, (5) identification of employees responsible for various aspects of development or commercialization of the product, and/or (6) identification of facilities used to manufacture, store or deliver the product. Further, the product information record may be associated with other records such as calendar records, commitment records, contact records, and/or central files records.

As used herein, the term "central files records" refers to information that describe, categorize, index and/or summarize documents. Central files records may thus provide brief descriptions of documents and may serve as the basis for locating documents through associated search functionality. Central files records may serve as the basis for locating documents based, for instance, on the identifying numbers contained in documents recorded in central files. The records may further include information identifying physical or electronic locations of documents. Central files may thus identify in which facility, office, storage room, shelf, box, or other location a requested document is currently stored or maintained, or identify an electronic storage location for the document, such as a URL address. In exemplary embodiments, central files records may also maintain a historical record of each document's location since its creation. In exemplary embodiments, the information contained within central files records may be linked to a representation of that document in a document management system, such as Livelink™, commercially available from OpenText Corporation or Documentum.

According to exemplary embodiments of the invention, the information stores may be interconnected allowing a user to manage regulatory data in a variety of ways. For example, if during a communication with a regulatory authority, a particular study is requested by the authority, the systems consistent with the invention may establish a contact record containing information about the request. Exemplary embodiments of the invention may then link such a contact record to a commitment record that sets forth the obligation to perform the study. Such contact and commitment records may be further linked to documents indexed within central files containing information pertaining to the study, e.g., protocols, materials, reports, etc. One or more of the above may also be linked to an information store containing calendar records or product information. Exemplary embodiments of the invention may thus generate data relationships between records stored in the plurality of interconnected information stores. Further, systems consistent with the invention may interconnect the information stores, as described above, by using data patterns shared among the information stores. For instance, a contact record may be interconnected or linked to a commitment record based on a common data pattern associated with the name or identification of a particular healthcare product.

Further, as described in more detail below, by interconnecting the information stores, systems consistent with the invention may make comparisons of any of the information contained within the stores across products, regulatory approvals and conditions, regions, time periods, etc.

FIG. 1 is a block diagram of one form of a regulatory data management system 100 consistent with the present invention. One skilled in the art will appreciate that system 100 may be implemented in a number of different configurations without departing from the scope of the present invention. In the embodiment shown in FIG. 1, system 100 may include a regulatory server 110, a plurality of client terminals 120-a to 120-n, a management terminal 130, and a network 140 for connecting server 110 with terminals 120 and 130. While FIG. 1 shows only one regulatory server 110, two client terminals 120 and one management terminal 130, system 100 may include any number of servers 110 and terminals 120, 130. Moreover, system 100 may be configured to not include any management terminal 130.

Regulatory server 110 may be a computing system that performs various functions. In one embodiment, server 110 may be configured to process requests received from client terminals 120-a to 120-n to retrieve regulatory data associated with one or more products. In response to user requests, server 110 may display regulatory data to users of terminals 120-a to 120-n, store regulatory data, manage the regulatory data, and process the regulatory data, such as by preparing regulatory reports.

In exemplary embodiments, server 110 may include the information stores (not shown in FIG. 1) for managing respective types of regulatory data requested by, for example, client terminals 120-a to 120-n. The information stores may be configured using any appropriate type of known storage system configuration that facilitates the storage of data, as well as the locating, accessing, and retrieving of data stored in the databases (e.g., Sybase, Oracle, MySQL, SQL, Access, etc. databases). Regulatory server 110 is described in greater detail below with respect to FIG. 2.

Client terminal 120 may be a computing system operated by a user. As shown in FIG. 1 (for simplicity, in terminal 120-a only), client terminal 120 may include, for example, a processor 122, a memory 124, a display device 126, and an interface device 128. Processor 122 may be one or more processor devices, such as a microprocessor, laptop computer, desktop computer, workstation, mainframe computer, etc., that execute program instructions to perform various functions. Memory 124 may be one or more storage devices that maintain data (e.g., instructions, software applications, etc.) used by processor 122. In one embodiment of the present invention, memory 124 may include browser software that enables client terminal 120-a to 120-n to transmit and retrieve regulatory data content from regulatory server 110 using a protocol such as HTML. Display device 126 may be any known type of display device that presents information to the user operating client terminal 120-a to 120-n. Interface device 128 may be one or more known interface devices modules that facilitate the exchange of data between the internal components of client terminal 120-a to 120-n and external components, such as server 110. In addition, interface device 128 may include a network interface device that allows client terminal 120-a to 120-n to receive and send data to and from network 140.

In embodiments employing a management terminal 130, terminal 130 may be a computing system operated by a system administrator. Alternately, these processes can be executed from client terminal 120-a to 120-n. Management terminal 130 may, for example, be a laptop computer, desktop computer, workstation, mainframe computer, etc. Through terminal 130, a system administrator may add, edit, inactivate, delete, or update relationships between regulatory data elements stored in regulatory server 110.

Network 140 may be any type of network that facilitates communication between remote components, such as server 110, client terminals 120, and management terminal 130. For example, network 140 may be a local area network (LAN), a wide area network (WAN), a virtual private network, a dedicated intranet, the Internet, and/or a wireless network.

One skilled in the art will appreciate that system 100 may be implemented in a number of different configurations without departing from the scope of the present invention. For example, components 110, 120, and 130 may be directly connected, as opposed to being connected via network 140. Further, additional components may be included in system 100, such as a connection to a regulatory authority (not shown) for exchanging regulatory data with regulatory server 110. In addition, client terminal 120 and/or management terminal 130 may be included within regulatory server 110, thus allowing server 110 to receive requests from a user operating server 110 itself.

Figure 2:
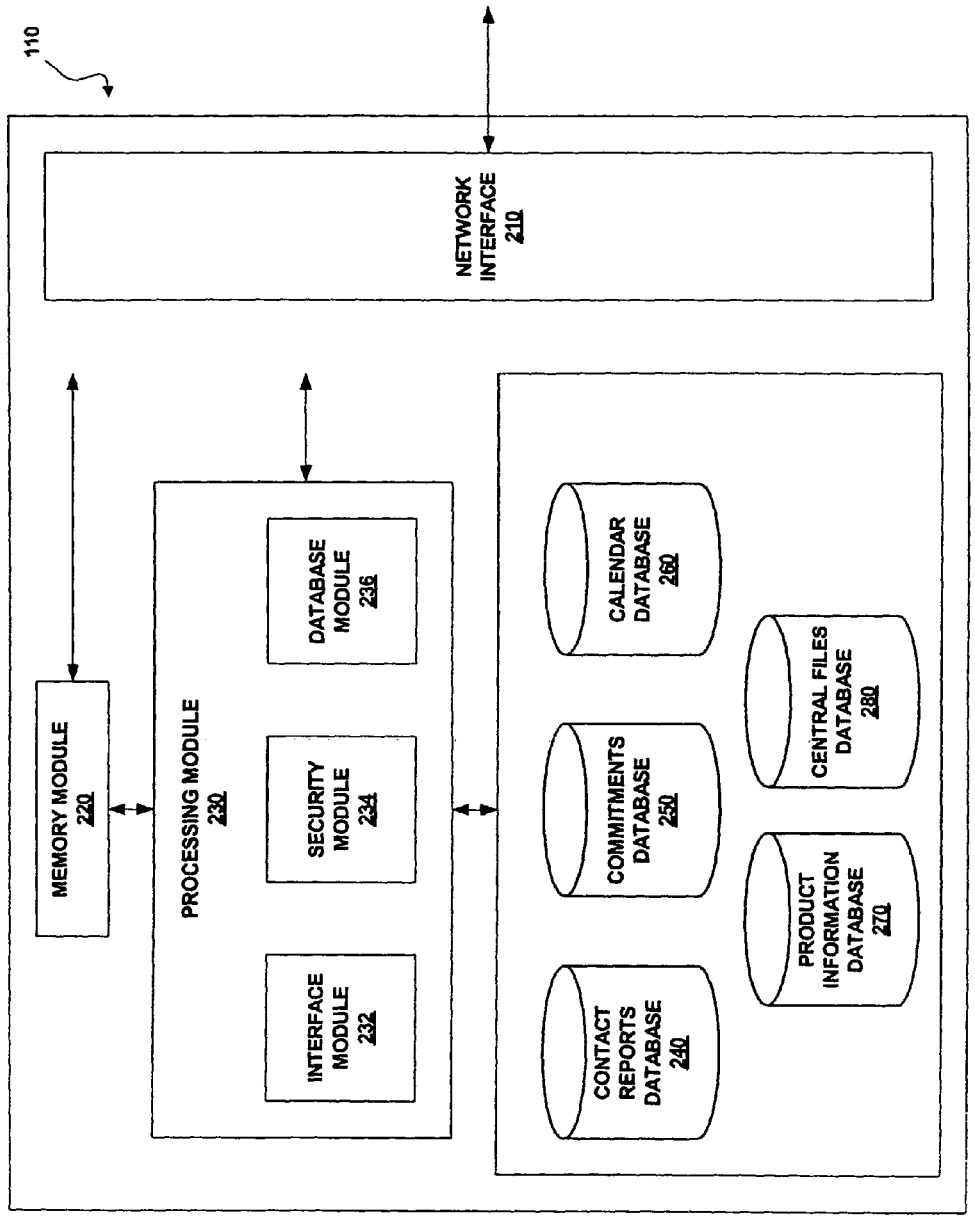
FIG. 2 illustrates an exemplary block diagram for a regulatory server, consistent with an embodiment of the present invention.

FIG. 2 is a block diagram of an exemplary embodiment of regulatory server 110 where the interconnected information stores are in the form of databases. As shown in FIG. 2, regulatory server 110 may further include a network interface 210, a memory module 220, a processing module 230, and the interconnected information store databases including, for example, a contact records database 240, a commitment records database 250, a calendar records database 260, a product information records database 270, and a central files records database 280.

Network interface 210 may be one or more devices that facilitate the transfer of information between server 110 and external components, such as client terminals 120. Network Interface module 210 may receive user requests from client terminal 120 or management terminal 130 and route those requests to processing module 230. In exemplary embodiments, network interface module 210 may be a web server that receives requests from terminals 120 and 130, forwards those requests to processing module 230, and returns the requested results to the requesting terminal 120 or 130 in the form of a web page.

Memory module 220 may represent one or more storage devices that maintain information that is used by processing module 230 and/or other components internal and external to regulatory server 110. Further, memory module 220 may include one or more programs that, when executed by an entity of processing module 230, perform one or more processes consistent with embodiments of the present invention. Examples of such processes are described in greater detail below, with respect to FIGS. 3 to 9. Memory module 220 may also include configuration data that may be used by processing module 230 to present user interface templates to client terminal 120 or management terminal 130.

Processing module 230, as shown in FIG. 2, may further include an interface module 232, a security module 234, and a database module 236. Interface module 232 may include components for preparing and presenting user interface templates to terminals 120 and 130 via network interface 210. As described above, interface module 232 may retrieve and process configuration data from memory module 220 in presenting user interface templates to client terminal 120 or management terminal 130 via network interface 210.

Security module 234 may include components for controlling user access to regulatory server 110, such as components for performing user authentication and authorization. In one implementation, user authentication may be performed via logon passwords. Other mechanisms for performing user authentication may be employed, such as a public key infrastructure (PKI) employing public key cryptography. Further, different users may be provided varying levels of authorization. For instance, certain users may be assigned different rights to server 110 based on a security profile assigned to each user. Each user, for example, may be assigned a security profile that may define: the functions the user may perform using server 110; the records associated with specific products the user may access or modify (e.g., read or write); and/or the interface templates which server 110 is to present to the user. In exemplary embodiments, memory module 220 may store the security profile associated with each respective user. Although depicted as part of regulatory server 110, all or part of the functionality of security module 234 may reside external to server 110. For example, client terminals 120 may control access to server 110 and server 110 may thus not include its own separate security component. Further, in preferred embodiments, security module 234 may also be used to apply a user's electronic signature when the user makes a modification to regulatory data stored in system 100. Preferred embodiments of the system may also include capturing an audit trail of all modifications to the data, as well as a means for centrally managing master data values used in the system.

Database module 236 may include components for controlling access to databases 240 to 280. For instance, database module 236 may include a search function that processes search query requests received by server 110, accesses the regulatory data in databases 240 to 280 in response to those requests, and retrieves the requested regulatory data for presentation, for example, to a user of client terminal 120 or management terminal 130.

As shown in FIG. 2, regulatory server 110 also includes a plurality of interconnected information stores. Contact records database 240 stores contact records, as described above. Commitment records database 250 stores commitment records, calendar records database 260 stores calendar records, product information records database 270 stores product information records, and central files records database 280 stores central file records, consistent with the above description of such records.

In some exemplary embodiments, regulatory data server 110 may generate data relationships between multiple levels of regulatory data stored in the interconnected information stores (e.g., databases 240 to 280). Each level may, for instance, pertain to a type of regulatory data. Server 110 may thus generate data relationships between the different data types with respect to, for example, a particular product or regulation. In this way, server 110 may generate data relationships between the following data types for a particular product or regulation: (1) contact report records of database 240 associated with respect to the particular product or regulation; (2) commitment records of database 250 associated with the particular product or regulation; (3) calendar records of database 260 associated with the particular product or regulation; (4) documents of product information database 270 associated with the particular product or regulation; and (5) documents in database 280 associated with the particular product or regulation. Server 110 may generate these data relationships based on common attributes included in the records of databases 240 to 280. Thus, when a user of client terminal 130 accesses a given document, server 110 may use these data relationships to present other documents of the various data types that relate to the same or similar product or regulation related to the document accessed by the user. Further, server 110 may also use these data relationships to sort regulatory data retrieved by a user according to the data attributes included in the records maintained by databases 240 to 280 (e.g., countries in which the product is approved for sale, product versions, regulations associated with the product, etc.).

Figure 3A:
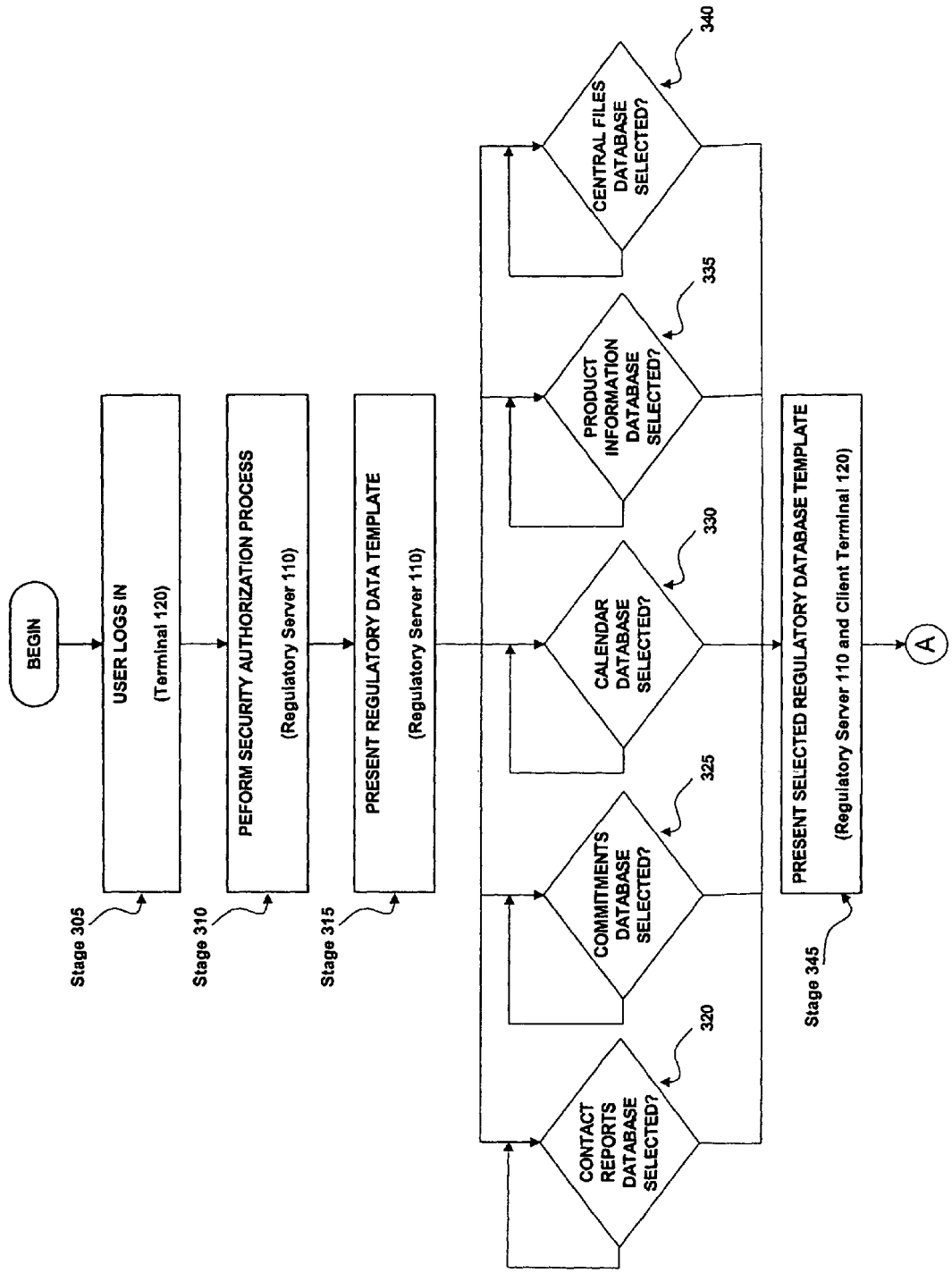
FIGS. 3(A) and 3(B) illustrate a flowchart of an exemplary regulatory data management process consistent with an embodiment of the invention.
Figure 3B:
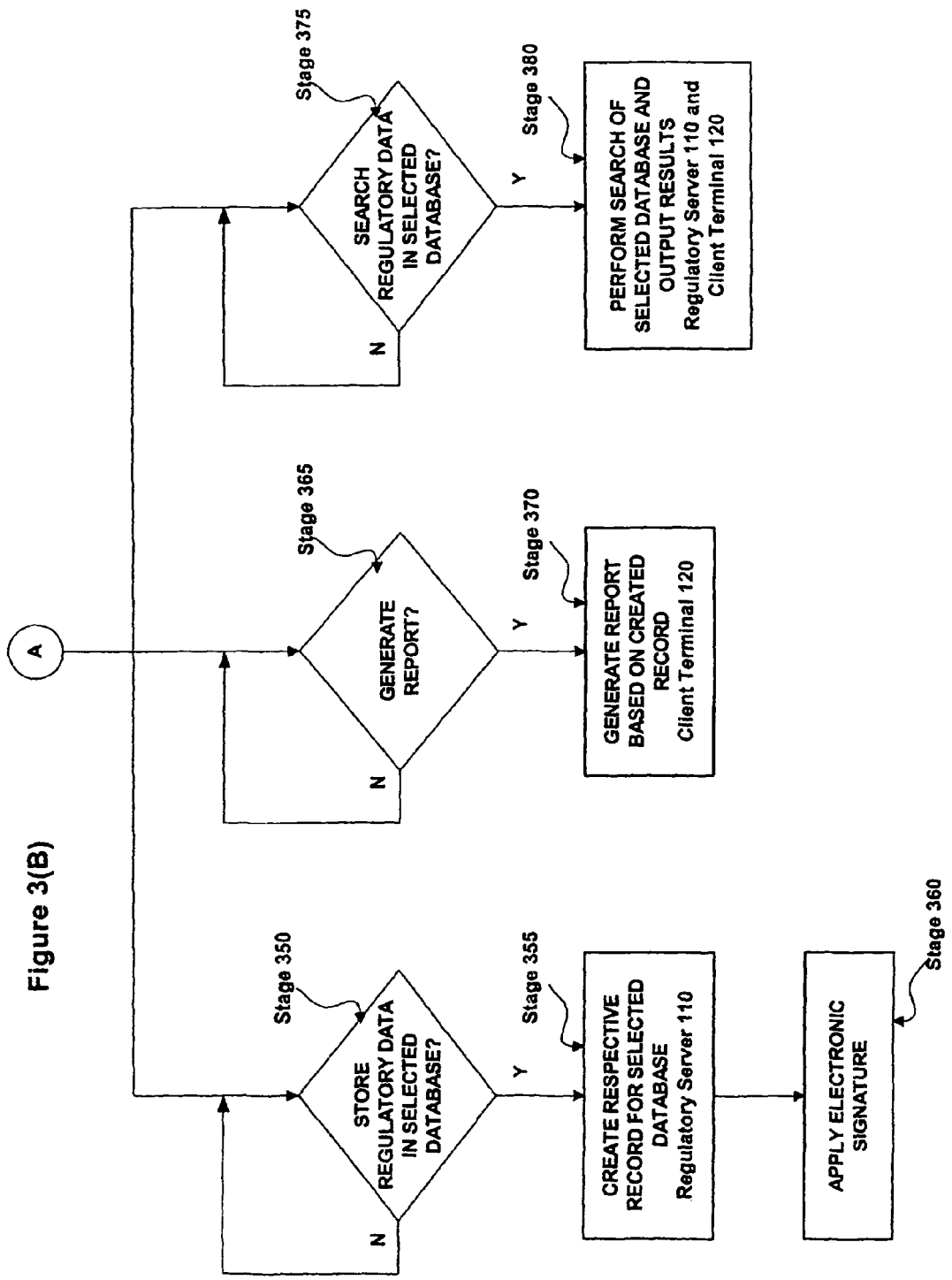

FIGS. 3A and 3B illustrate flowcharts for an exemplary regulatory data management process consistent with embodiments of the invention, such as the embodiments illustrated for system 100 in FIG. 1 and FIG. 2. As shown in the exemplary embodiment of FIG. 3(A), client terminal 120 may receive a command from a user to log into regulatory server 110 (stage 305). Client terminal 120 may execute the browser software in memory 124 to access regulatory server 110 via network 140 to retrieve a login prompt. The prompt may be in the form of a web page or similarly configured content. The format and configuration of the login prompt may vary and is not essential to the operation of this embodiment of the invention.

In one embodiment, regulatory server 110 may implement a security process that controls access to regulatory server 110 and its services (stage 310). For example, security module 234 may determine a security profile for the user upon the user logging into server 110. To this end, as described above, memory module 220 may access a security profile for each user of server 110 that may define which functions the user may access.

Once the user successfully logs in, regulatory server 110 may present a predetermined template that provides access to databases 240 to 280 (stage 315). In exemplary embodiments, as described above, server 110 may configure the template dependent upon the security profile of the particular user. For instance, if the user's security profile indicates that the user does not have authorization to access or modify certain regulatory records, then the presented template may be configured to not enable the user to perform such functions.

Figure 4A:
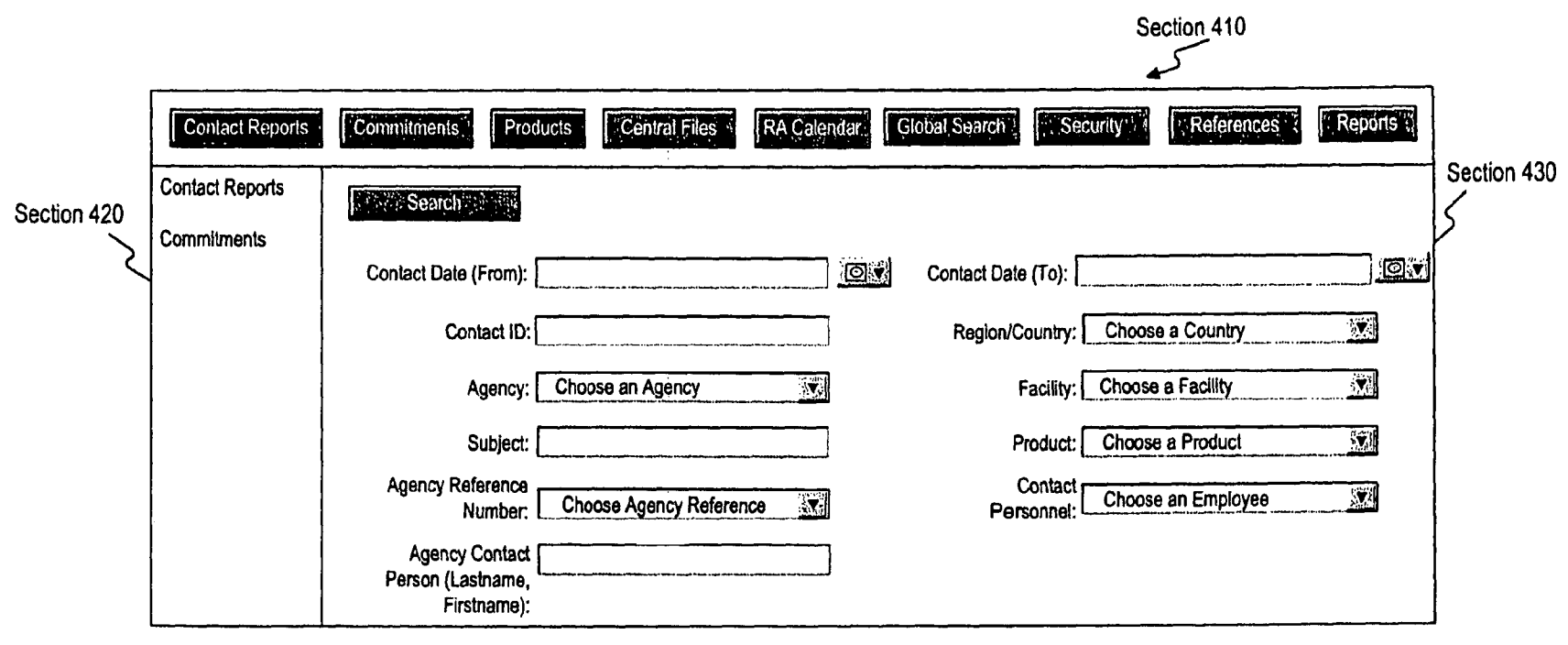
Figure 4B:
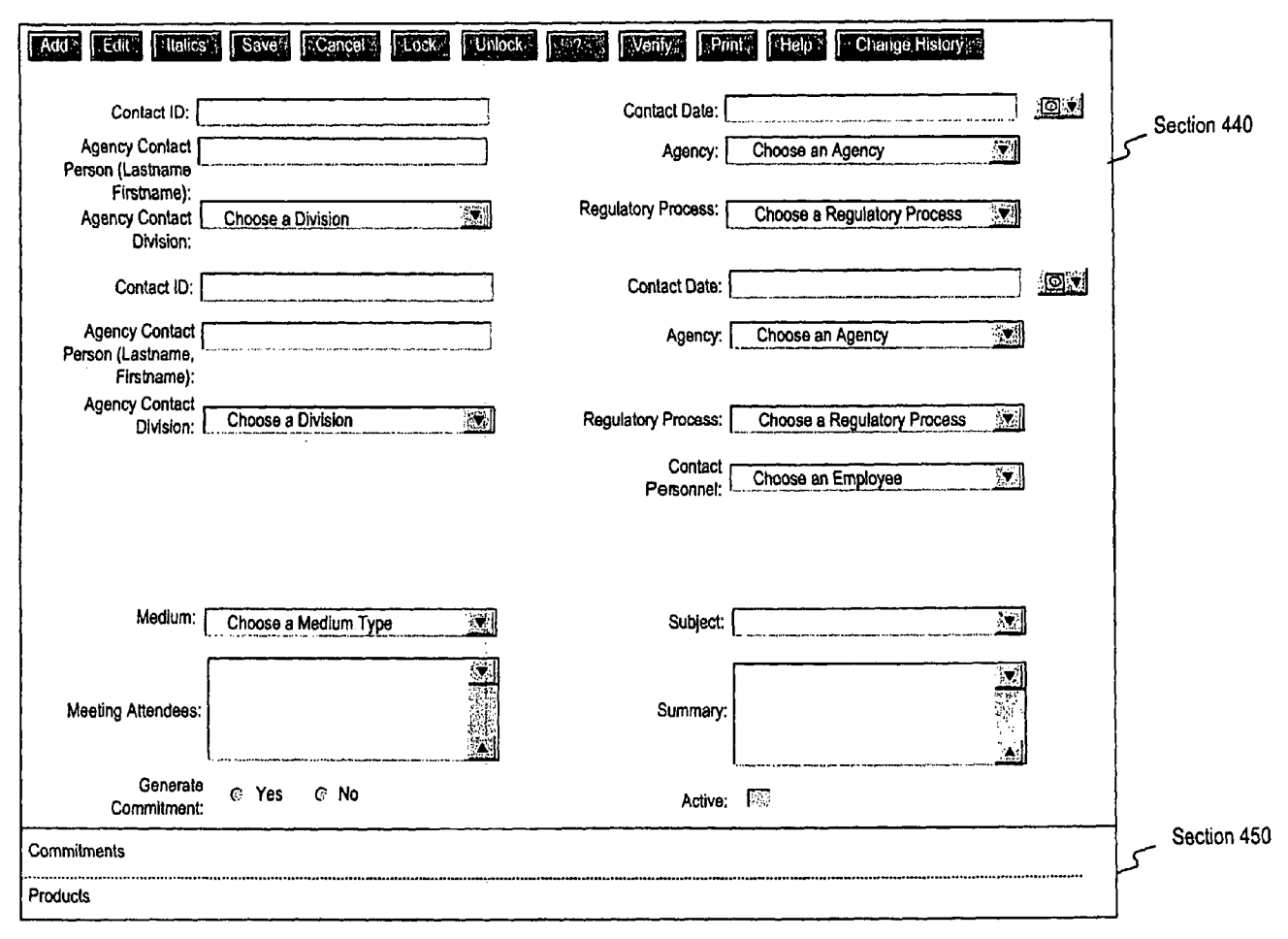

FIGS. 4(A) and 4(B) show an exemplary template 400 that may be provided by regulatory server 110. As shown in FIG. 4(A), template 400 may include several software implemented buttons section 410 (e.g., icons) that when selected activate a software process with respect to a particular one of databases 240 to 280. Template 400 may also include a navigation display section 420 for enabling the user to select various other interface templates corresponding to the software based button 410 selected by the user. For instance, if the user selects the button for contact records database 240, navigation section 420 may be configured to present options for selecting a "contact reports" or "commitments" template, as shown in FIG. 4(A).

Template 400 may also include a search display section 430 for enabling the user to formulate a search query with respect to a selected database. Further, as shown in FIG. 4(B), template 400 may include a data management display section 440 for enabling the user to compose or modify regulatory data for storage in a selected database, and a detail display section 450 for providing further details on types of regulatory data (e.g., a contact report or a commitment).

In the exemplary embodiment of FIG. 4, display sections 430 and 440 are configured for when a user has selected access to contact reports database 240. Section 430 thus enables the user to search contact reports database 240 by providing one or more parameters that the user may define to formulate a search query. To this end, section 430 may contain one or more parameter data fields associated with the regulatory contact data maintained by database 240. For instance, as shown in FIG. 4, section 430 may include fields for the following types of search parameters: (1) one or more "contact date" fields that allow the user to define date(s) of the contacts to be searched, (2) a "contact ID" field that allows the user to search by identification codes assigned to the contact, (3) "agency" and "agency reference number" fields that allow the user to search based on the regulatory authority associated with each contact, (4) "region/country," "facility," and "product" fields that allow the user to search based on information further identifying a particular product or regulation of interest, and (5) a "contact personnel" field that allows the user to search based on the personnel making the contact with the regulatory authority.

As also illustrated in the exemplary embodiment of FIG. 4(B), data management display section 440 may contain one or more parameter data fields associated with forming a contact record for storage in regulatory contacts database 240. For instance, section 440 may include fields for the following types of data: (1) a "contact date" field that allow the user to identify the date(s) of the contact, (2) a "contact ID" field that allows the user to assign an identification code to the contact, (3) "agency," "agency contact," and "agency contact division" fields that allow the user to identify the regulatory authority contacted, (4) a "contact personnel" field that allows the user to identify the personnel making the contact with the regulatory authority; and (5) additional fields that allow the user to provide information further identifying the particular contact, such as the communication medium, the subject of the contact, persons in attendance, a summary of the contact, whether a commitment was made, etc.

Figure 6:
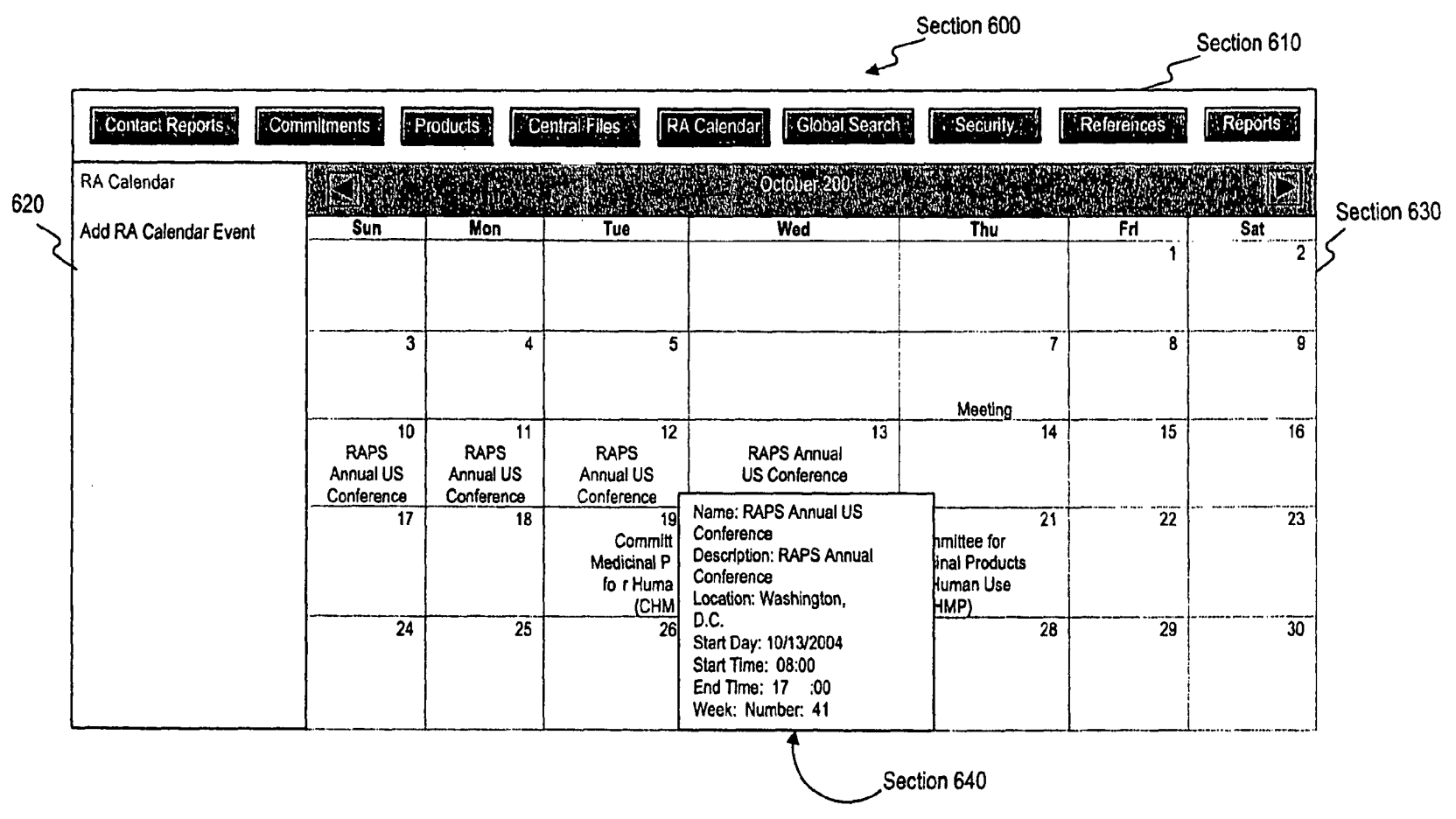
Figure 7B:
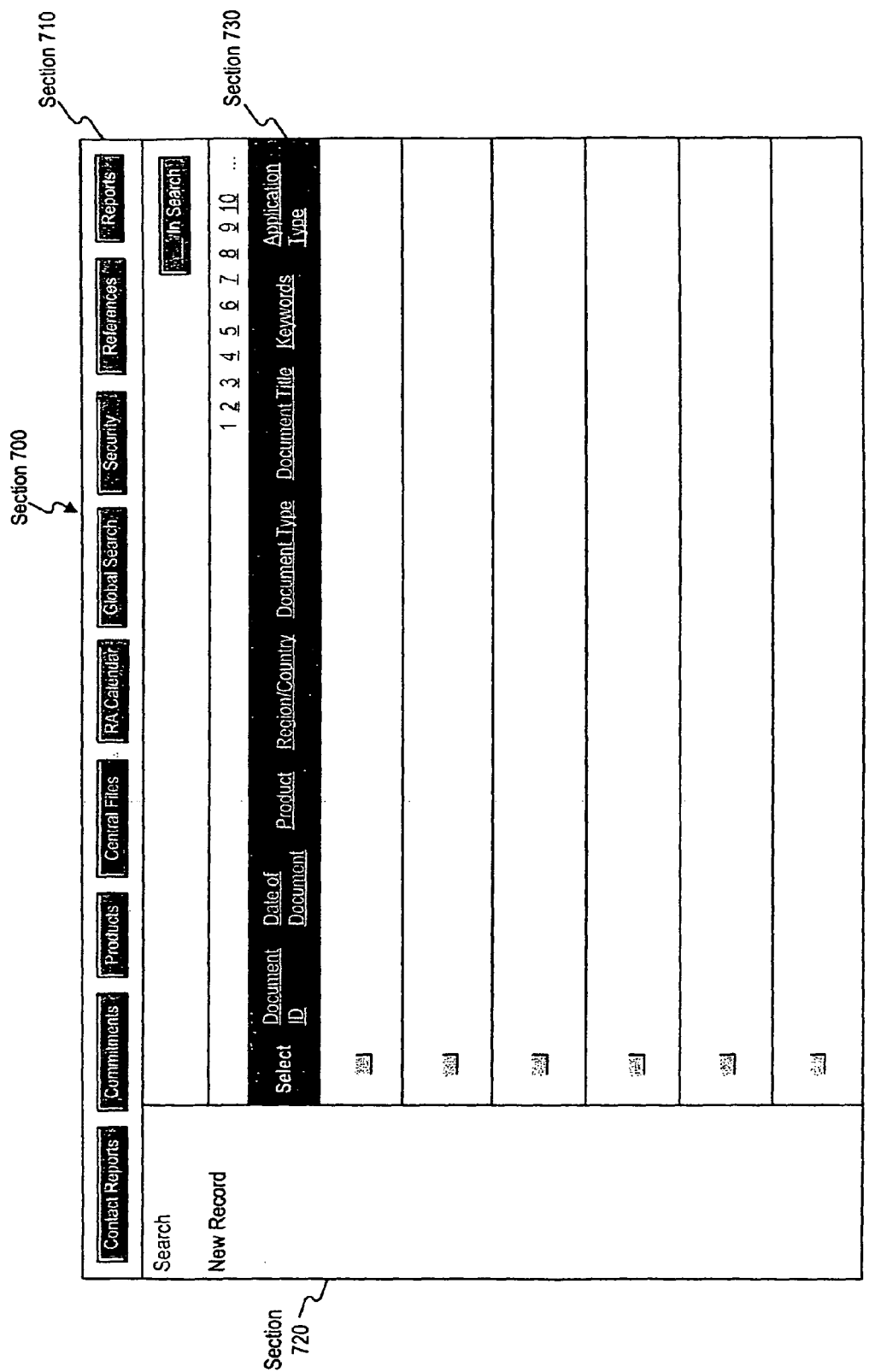

Although FIGS. 4(A) and 4(B) illustrate a template 400 for contact reports database 240, regulatory server 110 may present similar templates for the other databases. For instance, FIG. 5 illustrates an exemplary template 500 presented by server 110 when a user has selected product information database 270. As shown in FIG. 5, template 500 includes buttons section 510, a navigation section 520, a search section 530, and a data management section 540 similar to those described above with respect to FIG. 4. Server 110 may, however, display regulatory data via differently configured templates. For example, FIG. 6 illustrates an exemplary template 600 for calendar database 260. As shown in FIG. 6, template 600 may include buttons section 610, a navigation section 620, and a calendar 630 for displaying data associated with stored calendar records to the user. Further, FIG. 6 illustrates that template 600 may also be configured to display (e.g., at field 640) more detailed data of a calendar record upon the user selecting a particular record entry. Finally, FIGS. 7(A) and 7(B) illustrate an exemplary template 700 presented by server 110 when a user has selected central files database 280. As shown in FIG. 7, template 700 includes buttons section 710, a navigation section 720, a search section 730, and a data management section 740 similar to those described above with respect to FIG. 4.

Returning to FIG. 3(A), upon displaying the template to the user, regulatory server 110 may then determine whether the user has selected one of databases 240 to 280 via, for example, buttons section 410 (stages 320, 325, 330, 335, and 340). Based on which database the user may have selected, server 110 may then present a template configured for the selected database to client terminal 120 (stage 345). For instance, FIG. 4 illustrates an exemplary template for contact reports database 240, FIG. 5 illustrates an exemplary template for product information database 270, FIG. 6 illustrates an exemplary template for calendar database 260, and FIG. 7 illustrates an exemplary template for central files database 280.

As shown in FIG. 3(B), regulatory server 110 may then determine whether the user has chosen to enter or modify regulatory data for storage in the selected database (stage 350). As described above, a user may enter or modify a record or other data stored in one of databases 240 to 280 via, for example, the data management display section (e.g., sections 440, 540, or 740). Server 110 may then create a new record, or modify an existing record, for the regulatory data stored in the respective databases 240 to 280 selected by the user (stage 355), as well as store an audit trail for the modification of the record. Further, in preferred embodiments using interconnected information stores, entry of data into a database containing one type of records (e.g., contact records) may also prompt or cause the entry of data of that record into another type of record (e.g., a commitment record or central files record).

Once regulatory server 110 has created a record, server 110 may apply an electronic signature to the record (stage 360). In exemplary embodiments, server 110 may determine that an electronic signature is required to be appended to the record based, for example, on the security profile of the user maintained by security module 234 or on the type of created record (e.g., a record of central files database 280 may not require an electronic signature, while a contact record may require an electronic signature). In either event, client terminal 120 may prompt the user for the user's electronic or digital signature and then transmit the user's electronic or digital signature to server 110, whereupon security module 234 may then apply it to the created record. In this way, server 110 may ensure the accountability of the created record. While FIG. 3(B) shows that the electronic signature is applied after the record is created, systems consistent with the invention need not apply an electronic signature to the record, or need not apply an electronic signature in all cases. Moreover, other forms of data or process security may be used instead of or in addition to electronic signatures, such as, for example, data encryption techniques.

Based on the regulatory data entered via regulatory server 110, server 110 may allow a user to generate a search and report the results (stages 365 and 370). To this end, server 110 may present a search report template for display on a client terminal 120. FIGS. 8(A) and 8(B) illustrate an exemplary search report template 800 for presenting to client terminal 120. As shown in the figures, search report template 800 may include buttons section 810 and a navigation display section 820 listing the different search reports a user may generate. To generate a search report, the user may select a desired search report from navigation display section 820. The user will then be presented with a template that enables the user to enter various search report parameters. Upon then performing a search query of databases 240 to 280 for data to be included in the report, server 110 may display the search results and allow the user to export the search result data into a new application file (e.g., an HTML or Excel format file) for formatting the data or for creating a report.

Figure 9:
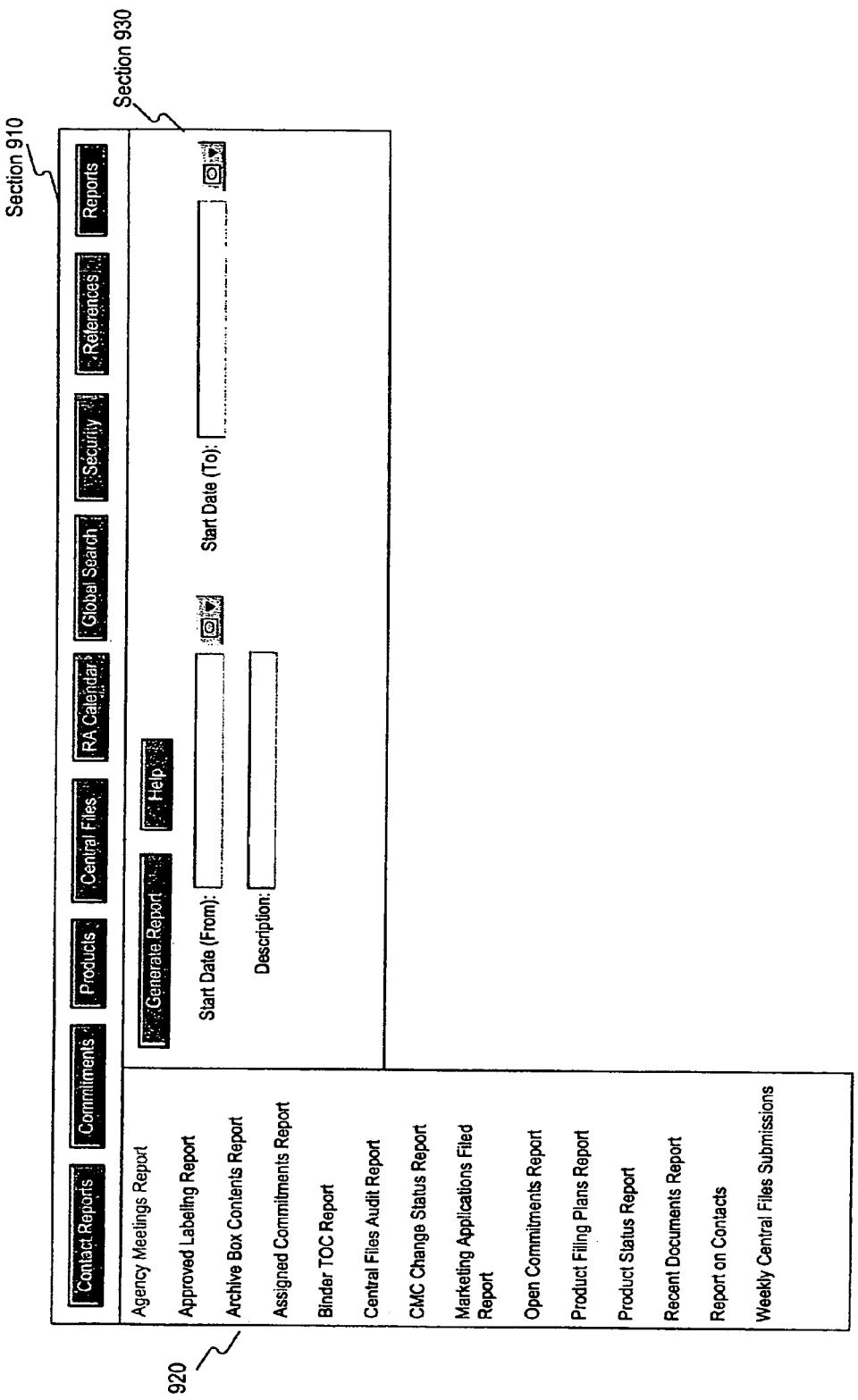
FIG. 9 illustrates an exemplary user interface template for a regulatory reports function, consistent with an embodiment of the present invention.

For example, to generate a contact record report, regulatory server 110 may retrieve the data of a contact record for exporting into a document template of a contact report. In particular, server 110 may populate data fields of the document template with corresponding data of the respective record. In this way, sever 110 may automatically generate a document template populated with information about a respective contact communication to thus build a report of the contact. The document template may include additional field(s) which the user may then insert further information about the contact communication. Further, in other embodiments, regulatory server 110 may also generate a link that associates the record with another document related to the contact communication. For instance, a contact record may be linked to a storage location in central files database 280 that may reference the location of a document associated with the contact communication for access by the user. Server 110 may similarly generate reports for other records of databases 250 to 280. In this regard, FIG. 9 illustrates an exemplary user interface template 900 for a generating a report based on the data of databases 240 to 280.

Further, in exemplary embodiments, regulatory server 110 may store a generated report document by using a unique number assigned to the report document. Server 110 may generate the serial number based upon, for example, a product family, a product name, application type, relevant country, and/or chronological sequence associated with the particular record.

As shown in FIG. 3(B), regulatory server 110 may also determine whether the user has chosen to search the regulatory data stored in the selected database (stage 375). As described above, a user may search data stored in one of databases 240 to 280 via, for example, the search display section. Server 110 may then search the records of databases 240 to 280 and output the search results to the user via, for example, client terminal 120 (stage 380). To this end, server 110 may present a search template to client terminal 120, such as search display section 430 described above with respect to FIG. 4. In exemplary embodiments, server 110 may allow a user to search each of databases 240 to 280 concurrently. In this regard, FIGS. 8(A) and 8(B) illustrate an exemplary user interface template 800 for a global search of all databases 240 to 280.

Accordingly, as described above, systems and methods are provided for managing regulatory data. The foregoing description of possible implementations consistent with the present invention does not represent a comprehensive list of all such implementations or all variations of the implementations described. The description of only some implementations should not be construed as intent to exclude other implementations. One of ordinary skill in the art will understand how to implement the invention in the appended claims in many other ways, using equivalents and alternatives that do not depart from the scope of the following claims.

The systems and methods disclosed herein may be embodied in various forms including, for example, a data processor, such as a computer that also includes a database. Moreover, the above-noted features and other aspects and principles of the present invention may be implemented in various environments. Such environments and related applications may be specially constructed for performing the various processes and operations according to the invention or they may include a general-purpose computer or computing platform selectively activated or reconfigured by code to provide the necessary functionality. The processes disclosed herein are not inherently related to any particular computer or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Systems and methods consistent with the present invention also include computer readable media that include program instruction or code for performing various computer-implemented operations based on the methods and processes of the invention. The media and program instructions may be those specially designed and constructed for the purposes of the invention, or they may be of the kind well known and available to those having skill in the computer software arts. Examples of program instructions include, for example, machine code, such as produced by a compiler, and files containing a high level code that can be executed by the computer using an interpreter.

What is claimed is:

1. A computer-implemented system for managing and accessing interconnected regulatory data associated with a regulatory status of a healthcare product of an entity, comprising:

a network interface configured to receive a plurality of types of regulatory data associated with the regulatory status of the healthcare product, wherein the plurality of types of regulatory data reflect interactions by the entity with a regulatory authority with respect to the healthcare product;

a plurality of information memory stores configured to store regulatory data records, each record including one or more of the plurality of types of regulatory data associated with the regulatory status of the healthcare product;

a computer processing module configured to:

establish data relationships between the plurality of types of regulatory data records, wherein the data relationships are used to interconnect the information memory stores;

maintain the interconnected information memory stores based on the data relationships between the plurality of types of regulatory data records associated with the regulatory status of the healthcare product, wherein the processing module is configured to maintain the interconnected information memory stores based on a common data pattern associated with a type of the healthcare product;

identify, in response to a received request, the interconnected regulatory data records associated with the regulatory status of the healthcare product stored in the interconnected information memory stores;

perform a first determination as to whether to generate, based upon the entry of regulatory data into a first regulatory data record stored in at least one of information memory stores, a second regulatory data record for storage in another of the information memory stores;

based on the first determination, generate the second regulatory data record;

perform a second determination as to whether a communication with a regulatory authority, recorded in a contact record, results in a commitment; and based on the second determination, link the contact record to a commitment record, said commitment record recording the commitment.

2. The system of claim 1, wherein the interconnected information stores comprise two or more of the following record types: calendar records, contact records, commitment records, product information records, and central files records.

3. The system of claim 2, wherein the contact records are digitally signed.

4. The system of claim 2, wherein the commitment records reflect commitments made to a regulatory authority associated with the healthcare product.

5. The system of claim 2, wherein the product information records include information pertaining to a third party involved in developing the healthcare product.

6. The system of claim 2, wherein the central files records are integrated with an external document management system.

7. The system of claim 1, wherein the processor further includes:
a database module that interconnects the plurality of information memory stores by using data patterns shared among the information memory stores.

8. The system of claim 1, wherein the processor generates the data relationships between records stored in the plurality of interconnected information memory stores.

9. The system of claim 1, wherein said processor further includes:
an interface module for retrieving, in response to the received request, configuration data used to present user interface templates from a memory module.

10. The system of claim 1, wherein the processor further includes a security module for configuring access by a user by assigning a user access rights to categories of information based on a security profile assigned to the user.

11. The system of claim 10, wherein the access rights reflect at least one of:
which functions the user may perform, what regulatory data the user may access, what requesting data the user may modify, or what user interface templates are presented to the user.

12. The system of claim 1, wherein the commitment includes an agreement to perform a product testing or an obligation to perform a study.

13. A computer-implemented method for managing and accessing interconnected regulatory data associated with a regulatory status of a healthcare product of an entity, comprising:
receiving, at a computer, a plurality of types of regulatory data associated with the regulatory status of the healthcare product, wherein the plurality of types of regulatory data reflect interactions by the entity with a regulatory authority with respect to the healthcare product;
storing, in a plurality of information memory stores of the computer, regulatory data records, each record including one or more of the plurality of types of regulatory data associated with the regulatory status of the healthcare product;
establishing data relationships between the plurality of types of regulatory data records, wherein the data relationships are used to interconnect the plurality of information memory stores;
maintaining, through use of a processor of the computer, the interconnected information memory stores based on the data relationships between the plurality of types of regulatory data records associated with the regulatory status of the healthcare product, including maintaining the interconnected information memory stores based on a common data pattern associated with a type of the healthcare product;
identifying, through use of the processor and in response to a received request, the interconnected regulatory data records associated with the regulatory status of the healthcare product stored in the interconnected information memory stores;
performing a first determination as to whether to generate, based upon the entry of regulatory data into a first regulatory data record stored in at least one of information memory stores, a second regulatory data record for storage in another of the information memory stores;
based on the first determination, automatically generating the second regulatory data record;
performing a second determination as to whether a communication with a regulatory authority, recorded in a contact record, results in a commitment; and
based on the second determination, linking the contact record to a commitment record, said commitment record recording the commitment.

14. The method of claim 13, wherein storing regulatory data in the interconnected information memory stores comprises storing two or more databases storing the following record types: calendar records, contact records, commitment records, product information records, and central files records.

15. The method of claim 14, further including:
digitally signing the contact records.

16. The method of claim 14, further including:
integrating the central files records with an external document management system.

17. The method of claim 13, further comprising:
interconnecting the plurality of information memory stores by using data patterns shared among the information memory stores.

18. The method of claim 13, further comprising:
generating the data relationships between records stored in the plurality of interconnected information memory stores.

19. The method of claim 13, further including:
retrieving, in response to the retrieved request, configuration data used to present user interface templates from a memory module.

20. The method of claim 12, further including:
configuring access by a user via a security module by assigning a user access rights to categories of information based on a security profile assigned to the user.

21. The computer-implemented method of claim 13, wherein the commitment includes an agreement to perform a product testing or an obligation to perform a study.

22. A non-transitory computer-readable storage medium including instructions for performing, when executed by a processor, a method for managing and accessing interconnected regulatory data associated with a regulatory status of a healthcare product of an entity, the method comprising:
receiving a plurality of types of regulatory data associated with the regulatory status of the healthcare product, wherein the plurality of types of regulatory data reflect interactions by the entity with a regulatory authority with respect to the healthcare product;
storing, in a plurality of information memory stores, regulatory data records, each record including one or more of the plurality of types of regulatory data associated with the regulatory status of the healthcare product;

establishing data relationships between the plurality of types of regulatory data records, wherein the data relationships are used to interconnect the information memory stores;

maintaining the interconnected information memory stores based on the data relationships between the plurality of types of regulatory data records associated with the regulatory status of the healthcare product, including maintaining the interconnected information memory stores based on a common data pattern associated with a type of the healthcare product;

identifying, in response to a received request, the interconnected regulatory data records associated with the regulatory status of the healthcare product stored in the interconnected information memory stores;

performing a first determination as to whether to generate, based upon the entry of regulatory data into a first regulatory data record stored in at least one of information memory stores, a second regulatory data record for storage in another of the information memory stores;

based on the first determination, automatically generating the second regulatory data record;

performing a second determination as to whether a communication with a regulatory authority, recorded in a contact record, results in a commitment; and based on the second determination, linking the contact record to a commitment record, said commitment record recording the commitment.

23. The non-transitory computer-readable storage medium of claim 22, wherein the commitment includes an agreement to perform a product testing or an obligation to perform a study.

* * * * *